United States Patent
Nielsen et al.

(10) Patent No.: US 10,577,568 B2
(45) Date of Patent: Mar. 3, 2020

(54) DETERGENT COMPOSITION

(75) Inventors: Lone Kierstein Nielsen, Lyngby (DK); Lise Munch Mikkelsen, Roedovre (DK); Esben Peter Friis, Herlev (DK); Juergen Carsten Franz Knoetzel, Copenhagen OE (DK); Ole Simonsen, Soeborg (DK)

(73) Assignee: Novozymes A/S (DK)

( * ) Notice: Subject to any disclaimer, the term of this patent is extended or adjusted under 35 U.S.C. 154(b) by 0 days.

(21) Appl. No.: 13/124,089

(22) PCT Filed: Nov. 11, 2009

(86) PCT No.: PCT/EP2009/064972
§ 371 (c)(1),
(2), (4) Date: Apr. 13, 2011

(87) PCT Pub. No.: WO2010/055052
PCT Pub. Date: May 20, 2010

(65) Prior Publication Data
US 2011/0212877 A1   Sep. 1, 2011

Related U.S. Application Data

(60) Provisional application No. 61/117,989, filed on Nov. 26, 2008.

(30) Foreign Application Priority Data

Nov. 13, 2008 (EP) ................................ 08169063

(51) Int. Cl.
*C11D 3/386* (2006.01)
*C07K 5/107* (2006.01)
*C11D 3/33* (2006.01)
*C11D 7/32* (2006.01)

(52) U.S. Cl.
CPC ............ *C11D 3/386* (2013.01); *C07K 5/1016* (2013.01); *C11D 3/33* (2013.01); *C11D 3/38663* (2013.01); *C11D 7/3245* (2013.01)

(58) Field of Classification Search
CPC .............. C11D 3/60; C11D 3/386; C07K 5/09
USPC ................. 510/226, 320, 392, 405
See application file for complete search history.

(56) References Cited

U.S. PATENT DOCUMENTS

| | | | | |
|---|---|---|---|---|
| 3,998,795 | A * | 12/1976 | Sarantakis | 530/311 |
| 4,568,476 | A * | 2/1986 | Kielman et al. | 510/226 |
| 5,861,366 | A * | 1/1999 | Ihns et al. | 510/320 |
| 6,165,966 | A * | 12/2000 | McIver et al. | 510/392 |
| 6,331,512 | B1 * | 12/2001 | Foote | C11D 3/08 510/226 |
| 2005/0232981 | A1 * | 10/2005 | Ben-Sasson | A61K 9/0014 424/448 |

FOREIGN PATENT DOCUMENTS

| | | |
|---|---|---|
| EP | 0 583 534 A1 | 2/1994 |
| WO | WO 94/04651 A1 | 3/1994 |
| WO | WO 95/25791 A1 | 9/1995 |
| WO | WO1995025791 A1 * | 9/1995 |
| WO | WO 98/13458 A1 | 4/1998 |
| WO | WO 2007/145963 A2 | 12/2007 |
| WO | WO2011/036153 * | 3/2011 |
| WO | WO-2011036153 A1 * | 3/2011 ......... C11D 3/38609 |

OTHER PUBLICATIONS

MSDS of ANTIPAIN peptide inhibitor pp. 1-3, 2019.*
Broadbridge et al., "First efficient synthesis of α-MAPI", Chem. Commun., pp. 1449-1450 (1998).
Galpin et al., "Synthetic analogues of the proteinase inhibitor: chymostatin", Int. J. Peptide Protein Res., vol. 23, pp. 477-486 (1984).
Sarubbi et al., "Peptide aldehydes as inhibitors of HIV protease", FEBS Letters, vol. 319, No. 3, pp. 253-256 (1993).

* cited by examiner

*Primary Examiner* — Gregory R Delcotto
*Assistant Examiner* — Preeti Kumar
(74) *Attorney, Agent, or Firm* — Eric J. Fechter

(57) ABSTRACT

Peptide aldehydes containing a ureido group are effective as stabilizers for protease in a detergent composition, and as stabilizers for a second enzyme in a liquid composition with a protease.

9 Claims, No Drawings

DETERGENT COMPOSITION

CROSS-REFERENCE TO RELATED APPLICATIONS

This application is a 35 U.S.C. 371 national application of PCT/EP2009/064972 filed Nov. 11, 2009, which claims priority or the benefit under 35 U.S.C. 119 of European application no. 08169063.8 filed Nov. 13, 2008 and U.S. provisional application no. 61/117,989 filed Nov. 26, 2008, the contents of which are fully incorporated herein by reference.

FIELD OF THE INVENTION

The present invention relates to a liquid detergent composition comprising a surfactant and a protease and to a liquid enzyme composition comprising a protease and optionally a second enzyme. More particularly, it relates to such compositions incorporating a compound which stabilizes the protease and/or the second enzyme. Further, the invention also relates to a stabilizing compound for use in such compositions.

BACKGROUND OF THE INVENTION

EP 0 583 534 A, WO 94/04651 A, WO 98/13458 A and WO 2007/145963 A describe enzyme stabilization in liquid detergent compositions comprising a reversible peptide aldehyde protease inhibitor. WO 95/25791 A describes methods for manufacturing protease enzymes using non-protein protease inhibitors.

α-MAPI, antipain, GE20372A and chymostatin A, B and C are described as peptide aldehydes with activity as protease inhibitors: R. J. Broadbridge et al., Chem. Commun. (1998), 1449. E. Sarubbi et al., FEBS Letters, 319 (3), 253-256 (1993). I. J. Galpin et al., Int. J. Peptide Protein Res., 23, 1984, 477-486.

SUMMARY OF THE INVENTION

The inventors have found that certain peptide aldehydes containing a "double N-capping group" (such as ureido (N—CO—N), oxamide (N—CO—CO—N), thioureido (N—CS—N), dithiooxamide (N—CS—CS—N) or thiooxamide (N—CS—CO—N) group) are effective as stabilizers for proteases in liquid enzyme formulations and in liquid detergent compositions, and as stabilizers for a second enzyme in a liquid composition with a protease. They also found that the peptide aldehydes can be released from the protease when the enzyme formulation or detergent composition is diluted with water.

Accordingly, the invention provides a detergent composition comprising a surfactant, a protease and a stabilizer of the formula:

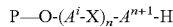

P—O-$(A^i$-X$)_n$-$A^{n+1}$-H wherein one X is the "double N-capping group" CO, CO—CO, CS, CS—CS or CS—CO (most preferably CO), and the other X'es are nothing (i.e., a chemical bond),
wherein n=1-10, preferably 2-5, most preferably 3
wherein i is an integer from 1 to n
wherein each $A^i$ and $A^{n+1}$ is an amino acid residue having the structure:
—NH—CR—CO— for a residue to the right of the double N-capping group, or
—CO—CR—NH— for a residue to the left of the double N-capping group wherein R is H— or an optionally substituted alkyl or alkylaryl group which may optionally include a hetero atom and may optionally be linked to the N atom, and
wherein P is hydrogen or any C-terminal protection group.

The invention also provides an enzyme composition, comprising a protease at a concentration of at least 0.1% by weight of enzyme protein and a stabilizer of the above formula.

Furthermore, the invention provides an enzyme composition, comprising a protease, a second enzyme and a stabilizer of the above formula.

Finally, the invention provides a stabilizer having the formula HO-$A^1$-CO-$A^2$-$A^3$-$A^4$-H, wherein $A^1$ is a Phe residue, $A^2$ is an Arg or Gly residue, $A^3$ is a Val or Gly residue, and $A^4$ is a Tyr residue.

DETAILED DESCRIPTION OF THE INVENTION

Stabilizer

The peptide aldehyde used as a protease stabilizer has the structure P—O-$(A^i$-X$)_n$-$A^{n+1}$-H with a "double N-capping group" X=CO, CO—CO, CS, CS—CS or CS—CO. It preferably contains four amino acid residues and preferably a ureido group (—NH—CO—NH—) between two of the residues. Thus, the structure is P—O-$A^1$-CO-$A^2$-$A^3$-$A^4$-H, P—O-$A^1$-$A^2$-CO-$A^3$-$A^4$-H or P—O-$A^1$-$A^2$-$A^3$-CO-$A^4$-H, where the amino acid residue(s) to the right of the ureido group has/have the structure —NH—CR—CO—, and the residue(s) to the left of the ureido group is/are inverted to —CO—CR—NH—.

$A^i$ and $A^{n+1}$, most preferably $A^1$ and/or $A^2$ and/or $A^3$ and/or $A^4$ may be a residue of an amino acid, e.g. an L-amino acid, particularly a naturally occurring amino acid, L-norleucine (Nle), L-norvaline (Nva) or capreomycidine (Cpd). In particular, $A^1$ may be Tyr, Leu, Phe, Met, Nle or Nva; $A^2$ may be Gly, Ala, Val, Arg, Leu or Cpd; $A^3$ may be Ala, Val, Gly, Leu, or Ile; and $A^4$ may be Phe, Tyr, Leu, Nva, Nle, Met or Arg.

P may be H— or the C-terminal protection group Me-, Et- or $CF_3$—

The stabilizer may have the formula HO-$A^1$-CO-$A^2$-$A^3$-$A^4$-H, e.g. the following compounds (where each amino acid is in the L-form unless indicated):

| Short name | $A^1$ | $A^2$ | $A^3$ | $A^4$ |
| --- | --- | --- | --- | --- |
| α-MAPI | Phe | Arg | Val | Phe |
| β-MAPI | Phe | Arg | Val | D-Phe |
| F—CO-RVY-H | Phe | Arg | Val | Tyr |
| F—CO-GGY-H | Phe | Gly | Gly | Tyr |
| F—CO-GAF-H | Phe | Gly | Ala | Phe |
| F—CO-GAY-H | Phe | Gly | Ala | Tyr |
| F—CO-GAL-H | Phe | Gly | Ala | Leu |
| F—CO-GA-Nva-H | Phe | Gly | Ala | Nva |
| F—CO-GA-Nle-H | Phe | Gly | Ala | Nle |
| Y—CO-RVY-H | Tyr | Arg | Val | Tyr |
| Y—CO-GAY-H | Tyr | Gly | Ala | Tyr |
| F—CS-RVF-H | Phe | Arg | Val | Phe |
| F—CS-RVY-H | Phe | Arg | Val | Tyr |
| F—CS-GAY-H | Phe | Gly | Ala | Tyr |

-continued

| Short name | A¹ | A² | A³ | A⁴ |
|---|---|---|---|---|
| Antipain | Phe | Arg | Val | Arg |
| GE20372A | Tyr | Arg | Val | Phe |
| GE20372B | Tyr | Arg | Val | D-Phe |
| Chymostatin A | Phe | Cpd | Leu | Phe |
| Chymostatin B | Phe | Cpd | Val | Phe |
| Chymostatin C | Phe | Cpd | Ile | Phe |

The stabilizer may be prepared by methods known in the art, e.g. as described by R. J. Broadbridge et al., Chem. Commun., 1998, 1449-1450; by P. Page et al., J. Org. Chem., 1999, 64, 794-799; or by I. J. Galpin et al., Int. J. Peptide Protein Res., 23, 1984, 477-486.

The molar ratio of the inhibitor to the protease may be 0.1:1 to 100:1, e.g. 0.5:1-50:1, 1:1-25:1 or 2:1-10:1.

Optional Second Stabilizer

Optionally, the enzyme or detergent composition may comprise one or more other protease stabilizers. Examples are boronic acid derivatives, organic acids, protein and peptide type inhibitors and peptide aldehydes, e.g. as described in WO 1995/029223, WO 1996/041859, WO 2006/045310, WO 2006/045310, WO 2007/113142, WO 2008/116915, WO 2009/095425 (patent application EP 08150977.0), WO 2009/118375 (patent application EP 08153299.6), WO 2007/145963, or WO 2007/141736.

Protease

The protease may be a serine, cysteine or aspartic protease. It may be an alkaline microbial protease, a trypsin-like protease or a subtilisin, e.g. a subtilisin derived from *Bacillus*. The protease may be subtilisin Novo, subtilisin Carlsberg, subtilisin BPN', subtilisin 309, subtilisin 147 and subtilisin 168 (described in WO 89/06279), trypsin (e.g. of porcine or bovine origin), the *Fusarium* protease described in WO 89/06270, a protease described in WO 1998/020115, WO 01/44452, WO 01/58275, WO 01/58276, WO 2003/006602, or WO 2004/099401, or it may have an amino acid sequence which is at least 90%, at least 95%, at least 98% or at least 99% identical to one of these.

Examples of commercially available proteases (peptidases) include Kannase™ Everlase™, Esperase™, Alcalase™, Neutrase™, Durazym™, Savinase™, Ovozyme™, Liquanase™, Polarzyme™, Pyrase™, Pancreatic Trypsin NOVO (PTN), Bio-Feed™ Pro and Clear-Lens™ Pro (all available from Novozymes A/S, Bagsvaerd, Denmark). Other commercially available proteases include Ronozyme™ Pro, Maxatase™, Maxacal™, Maxapem™, Opticlean™, Properase™, Purafect™, Purafect Ox™ and Purafact Prime™ (available from Danisco Genencor, Gist-Brocades, BASF, or DSM Nutritional Products).

Second Enzyme

In addition to the protease, the liquid composition may optionally comprise one or more other enzymes, e.g. selected among amylases, lipolytic enzymes (particularly lipases), cellulases, mannanases and oxidoreductases.

The amylase may be an alpha-amylase of bacterial or fungal origin, e.g. an alpha-amylase from *B. licheniformis*, described in GB 1,296,839. Commercially available amylases are Duramyl™, Termamyl™, Stainzyme™, Stainzyme Plus™, Termamyl Ultra™, Fungamyl™ and BAN™ (available from Novozymes A/S) and Rapidase™, Maxamyl P™, Purastar and Purastar OxAm (available from Gist-Brocades and Danisco Genencor).

The cellulase may be of bacterial or fungal origin. It may be a fungal cellulase from *Humicola insolens* (U.S. Pat. No. 4,435,307) or from *Trichoderma*, e.g. *T. reesei* or *T. viride*. Examples of cellulases are described in EP 0 495 257. Commercially available cellulases include Carezyme™, Celluzyme™, Endolase™, Celluclean™ (available from Novozymes), Puradax, Puradax HA, and Puradax EG (available from Danisco Genencor).

The oxidoreductase may be a peroxidase or an oxidase such as a laccase. The peroxidase may be of plant, bacterial or fungal origin. Examples are peroxidases derived from a strain of *Coprinus*, e.g., *C. cinerius* or *C. macrorhizus*, or from a strain of *Bacillus*, e.g., *B. pumilus*, particularly peroxidase according to WO 91/05858. Suitable laccases herein include those of bacterial or fungal origin. Examples are laccases from *Trametes*, e.g., *T. villosa* or *T. versicolor*, or from a strain of *Coprinus*, e.g., *C. cinereus*, or from a strain of *Myceliophthora*, e.g., *M. thermophila*.

The lipolytic enzyme may be a lipase or cutinase of bacterial or fungal origin. Examples include a lipase from *Thermomyces lanuginosus* (*Humicola lanuginosa*) described in EP 258 068 and EP 305 216, a *Rhizomucor miehei* lipase, e.g., as described in EP 238 023, a *Candida* lipase, such as a *C. antarctica* lipase, e.g., the *C. antarctica* lipase A or B described in EP 214 761, a *Fusarium oxysporum* lipase (WO 98/26057), a *Pseudomonas lipase* such as a *P. pseudoalcaligenes* and *P. alcaligenes* lipase, e.g., as described in EP 218 272, a *P. cepacia* lipase, e.g., as described in EP 331 376, a *P. stutzeri* lipase, e.g., as disclosed in BP 1,372,034, a *P. fluorescens* lipase, a *Bacillus lipase*, e.g., a *B. subtilis* lipase (Dartois et al., (1993), Biochemica et Biophysica acta 1131, 253-260), a *B. stearothermophilus* lipase (JP 64/744992), *B. pumilus* lipase (WO 91/16422), *Penicillium camenbertii* lipase (Yamaguchi et al., (1991), Gene 103, 61-67), the *Geotrichum candidum* lipase (Shimada, Y. et al., (1989), J. Biochem. 106, 383-388), and various *Rhizopus* lipases such as a *R. delemar* lipase (Hass, M. J et al., (1991), Gene 109, 117-113), a *R. niveus* lipase (Kugimiya et al., (1992), Biosci. Biotech. Biochem. 56, 716-719) and a *R. oryzae* lipase. Additional examples are cutinase from *Pseudomonas mendocina* (WO 88/09367), cutinase from *Fusarium solani pisi* (WO 90/09446) and cutinase from *Humicola insolens* (WO 2001/092502). The lipolytic enzyme may be a lipase variant, e.g. described in WO 2000/060063.

Examples of commercially available lipases include Lipex™, Lipoprime™, Lipopan™, Lipopan F™, Lipopan Xtra™, Lipolase™, Lipolase™ Ultra, Lipozyme™, Palatase™, Resinase™, Novozym™ 435 and Lecitase™ (all available from Novozymes A/S). Other commercially available lipases include Lumafast™ (*Pseudomonas mendocina* lipase from Danisco Genencor); Lipomax™ (*Ps. pseudoalcaligenes* lipase from Gist-Brocades or Danisco Genencor) and *Bacillus* sp. lipase from Solvay enzymes. Further lipases are available from other suppliers such as Lipase P "Amano" (Amano Pharmaceutical Co. Ltd.).

Examples of mannanases include Mannaway™ (product of Novozymes) and MannaStar (product of Danisco Genencor).

Sequence Identity

The degree of identity between two amino acid sequences is calculated as the number of exact matches in an alignment of the two sequences, divided by the length of the shorter of the two sequences. The result is expressed in percent identity. An exact match occurs when the two sequences have identical amino acid residues in the same positions of the overlap. The length of a sequence is the number of amino acid residues in the sequence.

The alignment of the two amino acid sequences may be determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

Alternatively, the alignment may be done by using the MegAlign program (version 7) developed by DNASTAR Inc., part of the Lasergene suite, based on Hein, J. J. (1990). "Unified approach to alignment and phylogenies." In Methods in Enzymology, Vol. 183: pp. 626-645. Using the Jotun Hein Method and the settings GAP PENALTY=11, GAP LENGTH PENALTY=3 for multiple alignments and KTUPLE=2 for pairwise alignments a series of percentage identity values can be calculated.

Detergent Composition

The detergent composition is a liquid composition. In addition to the protease, the composition may further comprise a second enzyme, particularly a lipase, an amylase, a cellulase or a carbohydrase.

The invention is particularly applicable to the formulation of liquid detergents where enzyme stability problems are pronounced. The liquid detergent may be aqueous, typically containing 5-95% water, e.g. 5-15% or 20-70% water and 0-20% organic solvent (hereinafter, percentages by weight).

The detergent comprises a surfactant which may be anionic, non-ionic, cationic, amphoteric or a mixture of these types. The detergent will usually contain 5-30% anionic surfactant such as linear alkyl benzene sulphonate (LAS), alpha-olefin sulphonate (AOS), alcohol ethoxy sulphate (AES) or soap. It may also contain 3-20% anionic surfactant such as nonyl phenol ethoxylate or alcohol ethoxylate.

The pH (measured in aqueous detergent solution) will usually be neutral or alkaline, e.g. 7-10. The detergent may contain 1-40% of a detergent builder such as zeolite, phosphate, phosphonate, citrate, NTA, EDTA or DTPA, or it may be unbuilt (i.e. essentially free of a detergent builder). It may also contain other conventional detergent ingredients, e.g. fabric conditioners, foam boosters, bactericides, optical brighteners and perfumes.

The detergent composition may be a fabric cleaning compositions, hard surface cleansing compositions, light duty cleaning compositions including dish cleansing compositions and automatic dishwasher detergent compositions.

The liquid detergent composition may comprise from about 0.0001% to about 10%, more particularly from about 0.00015% to about 1%, and most particularly from about 0.001% to about 0.1% of the inhibitor Thus, a stabilized liquid enzyme formulation typically contains 0.5-20% by weight, particularly 1-10% by weight, of enzyme protein (total of protease and optional second enzyme) and 0.01%-10% of the inhibitor, more particularly 0.05-5% by weight and most particularly 0.1%-2% by weight of the inhibitor.

A liquid detergent formulation will typically contain 0.04-400 micromolar enzyme (or 1-10000 mg EP/L), more particularly 0.16-160 micromolar enzyme (4-4400 mg EP/L) and most particularly 0.8-80 (20-2200 mg EP/L) and about 1-20 times more of the inhibitor, most particularly about 1-10 times more of the inhibitor.

The liquid detergent composition may contain water and other solvents as carriers. Low molecular weight primary or secondary alcohols exemplified by methanol, ethanol, propanol, and iso-propanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11. Finished products are typically formulated at this range. Techniques for controlling pH at recommended usage levels include the use of, for example, buffers, alkalis, and acids. Such techniques are well known to those skilled in the art.

When formulating the hard surface cleaning compositions and fabric cleaning compositions of the present invention, the formulator may wish to employ various builders at levels from about 5% to about 50% by weight. Typical builders include the 1-10 micron zeolites, polycarboxylates such as citrate and oxydisuccinates, layered silicates, phosphates, and the like. Other conventional builders are listed in standard formularies.

EXAMPLES

Example 1

Various peptide aldehydes of the invention were produced by a custom peptide synthesis company, all with a purity >80%. The peptide aldehydes were dissolved in DMSO to a concentration of 10 mg/ml before use.

A model liquid detergent A was prepared for testing the various stabilizers:

| Component | % w/w |
|---|---|
| Sodium alkylethoxy sulphate (C9-15, 2EO) | 6.0 |
| Sodium dodecyl benzene sulphonate | 3.0 |
| Sodium toluene sulphonate | 3.0 |
| Oleic acid | 2.0 |
| Primary alcohol ethoxylate (C12-15, 7EO) | 3.0 |
| Primary alcohol ethoxylate (C12-15, 3EO) | 2.5 |
| Ethanol | 0.5 |
| Monopropylene glycol | 2.0 |
| Tri-sodium citrate 2H$_2$O | 4.0 |
| Triethanolamine | 0.4 |
| Protease (Savinase 16 LEX) | 0.5 |
| Lipase (Lipex 100 L) | 0.5 |
| De-ionized water | Ad 100% |
| pH adjusted to 8.5 with NaOH | |

Further, the following detergents were prepared by adding stabilizers to detergent A:

| Detergent ID | Detergent A | Stabilizer (from a 10 mg/ml solution) | Molar ratio of inhibitor relative to protease |
|---|---|---|---|
| B | 100 g | 1.5 mg F—CO-RVF-H | 3 |
| C | 100 g | 2.5 mg F—CO-RVF-H | 5 |
| D | 100 g | 5.0 mg F—CO-RVF-H | 10 |
| E | 100 g | 1.5 mg F—CO-RVY-H | 3 |
| F | 100 g | 2.6 mg F—CO-RVY-H | 5 |
| G | 100 g | 5.1 mg F—CO-RVY-H | 10 |
| H | 100 g | 1.2 mg F—CO-GGY-H | 3 |
| J | 100 g | 2.0 mg F—CO-GGY-H | 5 |
| K | 100 g | 3.9 mg F—CO-GGY-H | 10 |

The detergents were placed in closed glasses at 35° C. and 40° C. Residual activity of lipase and protease was measured (by comparison to a reference stored at −18° C.) at different times, using standard enzyme analytical methods available at Novozymes (protease measured by hydrolysis of N,N-dimethylcasein at 40° C., pH 8.3 and lipase measured by hydrolysis of p-nitrophenyl valerate at 40° C., pH 7.7).

| % residual activity<br>Detergent | Residual protease activity | | Residual lipase activity |
|---|---|---|---|
| | 4 weeks 35° C. | 1 week 40° C. | 1 week 35° C. |
| A (reference) | 20 | 11 | 3 |
| B (F—CO-RVF-H, 3x) | | 63 | 22 |
| C (F—CO-RVF-H, 5x) | | 83 | 51 |
| D (F—CO-RVF-H, 10x) | | 78 | 69 |
| E (F—CO-RVY-H, 3x) | 62 | 55 | 17 |
| F (F—CO-RVY-H, 5x) | 81 | 75 | 53 |
| G (F—CO-RVY-H, 10x) | 86 | 81 | 69 |
| H (F—CO-GGY-H, 3x) | 26 | 17 | 3 |
| J (F—CO-GGY-H, 5x) | 31 | 20 | 4 |
| K (F—CO-GGY-H, 10x) | 38 | 28 | 5 |

From this example it is clear that the peptide aldehydes of the invention are very efficient as protease stabilizers and as stabilizers for a second enzyme in the presence of a protease.

The invention claimed is:

1. A liquid automatic dishwashing detergent composition comprising a surfactant, a protease and a peptide aldehyde of the formula P-O-A$^1$-CO-A$^2$-A$^3$-A$^4$-H wherein
P is H, Me, Et or CF$_3$;
A$^1$ is a residue of Tyr, Leu, Phe, Met, Nle or Nva;
A$^2$ is a residue of Gly, Ala, Val, Arg, Leu or Cpd;
A$^3$ is a residue of Val, Gly, Leu or Ile;
A$^4$ is a residue of Phe, Tyr, Leu, Nva, Nle, Met or Arg, wherein CO is a double N-capping group.

2. The composition of claim 1, wherein the peptide aldehyde has the formula Phe-CO-Arg-Val-Phe-H, Phe-CO-Arg-Val-Tyr-H or Phe-CO-Gly-Gly-Tyr-H.

3. The composition of claim 1, which further comprises a second enzyme selected from the group consisting of lipase, amylase, cellulase, and carbohydrase.

4. The composition of claim 1, wherein the protease is an alkaline protease, an aspartic protease, a serine protease, a cysteine protease, or a subtilisin.

5. A liquid enzyme automatic dishwashing detergent composition, comprising a protease at a concentration of at least 0.1% by weight of enzyme protein and a compound of the formula P-O-A$^1$-CO-A$^2$-A$^3$-A$^4$-H wherein
P is H, Me, Et or CF$_3$;
A$^1$ is a residue of Tyr, Leu, Phe, Met, Nle or Nva;
A$^2$ is a residue of Gly, Ala, Val, Arg, Leu or Cpd;
A$^3$ is a residue of Val, Gly, Leu or Ile;
A$^4$ is a residue of Phe, Tyr, Leu, Nva, Nle, Met or Arg, wherein CO is a double N-capping group.

6. A liquid enzyme automatic dishwashing detergent composition, comprising a protease, a second enzyme and a compound of the formula P-O-A$^1$-CO-A$^2$-A$^3$-A$^4$-H wherein
P is H, Me, Et or CF$_3$;
A$^1$ is a residue of Tyr, Leu, Phe, Met, Nle or Nva;
A$^2$ is a residue of Gly, Ala, Val, Arg, Leu or Cpd;
A$^3$ is a residue of Val, Gly, Leu or Ile;
A$^4$ is a residue of Phe, Tyr, Leu, Nva, Nle, Met or Arg, wherein CO is a double N-capping group.

7. The composition of claim 1, wherein molar ratio of peptide aldehyde to protease is 0.1:1.

8. The composition of claim 1, wherein molar ratio of peptide aldehyde to protease is 100:1.

9. The composition of claim 1, wherein molar ratio of peptide aldehyde to protease is 0.5:1 to 50:1.

* * * * *